(12) United States Patent
Maa et al.

(10) Patent No.: US 11,850,316 B2
(45) Date of Patent: Dec. 26, 2023

(54) SELF-DISINFECTING PHOTOCATALYST SHEET WITH PRIMER

(71) Applicant: Aleddra Inc., Renton, WA (US)

(72) Inventors: Chia-Yiu Maa, Bellevue, WA (US); Li-Jyuan Luo, Taipei (TW); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 196 days.

(21) Appl. No.: 17/352,296

(22) Filed: Jun. 19, 2021

(65) Prior Publication Data

US 2022/0088235 A1 Mar. 24, 2022

Related U.S. Application Data

(63) Continuation-in-part of application No. 17/027,535, filed on Sep. 21, 2020.

(51) Int. Cl.
| | | |
|---|---|---|
| *A61L 2/00* | (2006.01) | |
| *B01J 35/02* | (2006.01) | |
| *B01J 21/10* | (2006.01) | |
| *C09J 7/22* | (2018.01) | |
| *C09J 7/29* | (2018.01) | |
| *C08K 3/08* | (2006.01) | |
| *A61L 2/08* | (2006.01) | |
| *B01J 35/00* | (2006.01) | |

(Continued)

(52) U.S. Cl.
CPC .............. *A61L 2/088* (2013.01); *B01J 21/063* (2013.01); *B01J 23/10* (2013.01); *B01J 23/50* (2013.01); *B01J 35/004* (2013.01); *B01J 35/02* (2013.01); *B01J 37/0215* (2013.01); *C08K 3/08* (2013.01); *C09J 7/22* (2018.01); *C09J 7/29* (2018.01); *C08K 2003/2241* (2013.01); *C08K 2201/005* (2013.01); *C08K 2201/014* (2013.01); *C09J 2301/41* (2020.08); *C09J 2400/143* (2013.01)

(58) Field of Classification Search
None
See application file for complete search history.

(56) References Cited

U.S. PATENT DOCUMENTS

| | | | |
|---|---|---|---|
| 9,522,384 B2 * | 12/2016 | Lu | ............................ B01J 37/036 |
| 2013/0196146 A1 * | 8/2013 | Yu | .............................. B32B 7/12 |
| | | | 156/60 |
| 2014/0004331 A1 * | 1/2014 | Hida | ......................... B32B 27/36 |
| | | | 428/323 |

OTHER PUBLICATIONS

"The Antibacterial Mechanism of Silver Nanoparticles and Its Application in Dentistry"; International Journal of Nanomedicine 2020: 15 2555-2562 (Year: 2020).*

* cited by examiner

*Primary Examiner* — Frank D Ducheneaux
(74) *Attorney, Agent, or Firm* — Han IP PLLC; Andy M. Han

(57) ABSTRACT

A self-disinfecting photocatalyst sheet includes a substrate material and a photocatalyst layer with a primary photocatalyst and a secondary photocatalyst. The primary photocatalyst is a metal oxide photocatalyst, whereas the secondary photocatalyst is a metallic photocatalyst. The substrate material binds the photocatalyst layer by either connecting a metal ion of the primary photocatalyst and/or the secondary photocatalyst through two oxygen atoms of a carboxyl group (COO), or by forming hydrogen bonds between a carbonyl group and a surface hydroxyl group (OH$^-$) of the primary photocatalyst. The self-disinfecting photocatalyst sheet is activatable by a visible light and can self-disinfect against bacteria and viruses.

6 Claims, 2 Drawing Sheets

(51) Int. Cl.
*B01J 21/06* (2006.01)
*B01J 23/50* (2006.01)
*B01J 37/02* (2006.01)
*B01J 23/10* (2006.01)
*C08K 3/22* (2006.01)

SELF-DISINFECTING PHOTOCATALYST SHEET WITH PRIMER

CROSS-REFERENCE TO RELATED PATENT APPLICATION(S)

The present disclosure is a continuation-in-part (CIP) of U.S. patent application Ser. No. 17/027,535, filed 21 Sep. 2020, the content of which being incorporated by reference in its entirety herein.

BACKGROUND

Technical Field

The present disclosure pertains to the field of antimicrobial photocatalyst device and, more specifically, proposes a self-disinfecting photocatalyst sheet with primer.

Description of Related Art

In U.S. patent application Ser. No. 17/027,535, a self-disinfecting photocatalyst sheet was introduced. It includes a substrate material and a photocatalyst layer with a primary photocatalyst and a secondary photocatalyst. The primary photocatalyst is a metal oxide photocatalyst, whereas the secondary photocatalyst is a metallic photocatalyst. The primary photocatalyst forms a covalent bond with the substrate material. The self-disinfecting photocatalyst sheet is activatable by a visible light and can self-disinfect against bacteria and viruses. Also introduced in U.S. patent application Ser. No. 17/027,535 is a sol-gel coating process where a water-based photocatalyst solution is spray-coated over the first side of the two surfaces of the substrate material, followed by a curing process and perhaps another coating processing of an adhesive layer on the second side of the substrate material. One area that was not properly addressed U.S. patent application Ser. No. 17/027,535 is the means to improve and secure the binding of the photocatalyst onto the substrate material to prevent the wear-and-tear of the photocatalyst layer, and subsequently the antimicrobial effectiveness of the self-disinfecting photocatalyst sheet.

The biding of binding of the photocatalyst onto the substrate material can be improved before, during, or after the spray-coating process of the water-based photocatalyst solution unto the substrate material. Before the spray-coating process, a low-temperature air atmospheric plasma or a corona treatment may be applied to the first side of the substrate material to improve its hydrophilic property by creating higher surface energy and increasing polar groups or oxidized functional groups, such as C—OH, C=O, COOH, C—O—C, and hydroperoxide, on the first side of the substrate material. During the spray-coating process, a water-soluble primer may be used to create hydrogen bonds with the first side of the substrate material. Moreover, the primer can bind strongly with the photocatalyst (e.g., $TiO_2$) via either the connection of ion $Ti^{4+}$ with two oxygen atoms of carboxyl group or by forming hydrogen bonds between the carbonyl group and the surface hydroxyl group ($OH^-$) of $TiO_2$. After the spray-coating process, a curing process may be followed, as introduced in U.S. patent application Ser. No. 17/027,535.

If a water-soluble primer is used during the spray-coating process of the water-based photocatalyst solution unto the substrate material, the structure characteristic of the carboxyl group or the carbonyl group can still be observed in the final self-disinfecting photocatalyst sheet, even though the original primer material is unidentifiable. The present disclosure proposes a self-disinfecting photocatalyst sheet that contains a primer structure characteristic along the boundary where the photocatalyst layer meets the substrate material.

SUMMARY

In one aspect, a self-disinfecting photocatalyst sheet comprises a substrate material and a photocatalyst layer. The substrate material has a first side and a second side. The photocatalyst layer contains a primary photocatalyst and a secondary photocatalyst. The primary photocatalyst is a metal oxide photocatalyst, whereas the secondary photocatalyst is a metallic photocatalyst. The mass ratio of the primary photocatalyst to the secondary photocatalyst is 10:1 to 100:1. With the mass ratio, the metallic photocatalyst is appropriately categorized as a secondary photocatalyst, and should not be considered as a co-photocatalyst to the primary photocatalyst, for it does not contribute the photocatalytic activities at the same level as that of the primary photocatalyst.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of the primary, the secondary photocatalyst, the substrate material, and the hydrophilic primer.

The present disclosure discloses a self-disinfecting photocatalyst sheet includes a substrate material and a photocatalyst layer with a primary photocatalyst and a secondary photocatalyst. The primary photocatalyst is a metal oxide photocatalyst, whereas the secondary photocatalyst is a metallic photocatalyst. The substrate material binds the photocatalyst layer by either connecting the primary photocatalyst and/or the secondary photocatalyst through two oxygen atoms of a carboxyl group, or by forming hydrogen bonds between a carbonyl group and a surface hydroxyl group ($OH^-$) of the primary photocatalyst. The self-disinfecting photocatalyst sheet is activatable by a visible light and can self-disinfect against bacteria and viruses.

One novel feature of the present disclosure is on how the substrate material connects with the photocatalyst layer. The substrate material may bind the photocatalyst layer by connecting a metal ion of the primary photocatalyst and/or the secondary photocatalyst through two oxygen atoms of a carboxyl group (COO). FIG. 1a shows such an example where a with primer the carboxyl group can bind strongly with a $TiO_2$ metal oxide primary photocatalyst via the connection of an ion $Ti^{4+}$ with two oxygen atoms of the carboxyl group (COO—$Ti^{4+}$). The ion $Ti^{4+}$ may be replaced with $Ag^+$ (as shown in FIG. 1b), $Ce^{3+}$ (as shown in FIG. 1c), $Au^{2+}$, $Cu^{2+}$, $Fe^{2+}$, or $Zn^{2+}$ when they are used as the metallic secondary photocatalyst. Alternatively, the substrate material may bind the photocatalyst layer by forming hydrogen bonds between a carbonyl group and a surface hydroxyl group ($OH^-$) of the primary photocatalyst, as shown in FIG. 2 when using $TiO_2$ as the metal oxide primary photocatalyst.

Figure 1:
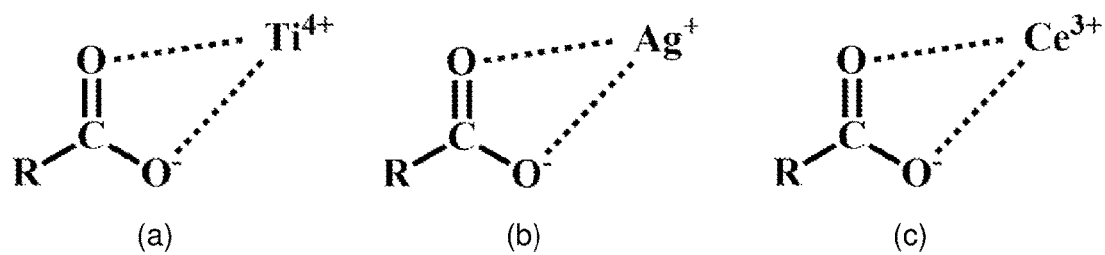
FIG. 1 schematically depicts the binding of a substrate material R via two oxygen atoms of a carboxyl group (COO) to an ion $Ti^{4+}$, an ion $Ag^+$, and an ion $Ce^{3+}$.
Figure 2:
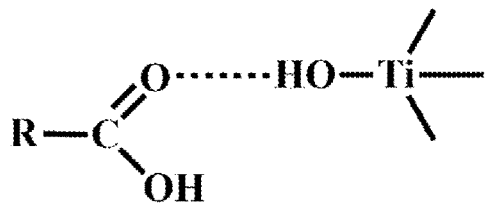
FIG. 2 schematically depicts the binding of a substrate material R via a carbonyl group and a surface hydroxyl group ($OH^-$) of $TiO_2$.
Figure 3:
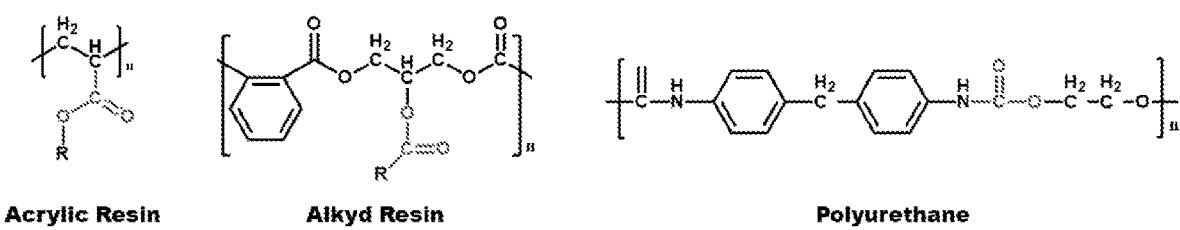
FIG. 3 schematically depicts the functional group of acrylic resin, alkyd resin, and polyurethane with the carboxyl groups highlighted in red.

The carboxyl group for binding ion $Ti^{4+}$ shown in FIG. 1 or the carbonyl group for binding the surface hydroxyl group ($OH^-$) of $TiO_2$ shown in FIG. 2 may not be part of the natural structure of the substrate material. Rather, they are introduced into the surface structure of the substrate material using some hydrophilic primer, such as acrylic polymers (acrylic resin), alkyd polymers (alkyd resin), and polyurethanes. FIG. 3 shows the functional group of acrylic resin, alkyd resin, and polyurethane with the carboxyl groups highlighted in red.

In some embodiments, an adhesive layer is coated on the second side of the substrate material such that the present disclosure may adhere to a surface for providing self-disinfection protection for that surface.

In some embodiments, the primary metal oxide photocatalyst includes anatase titanium dioxide ($TiO_2$) because the anatase-type titanium (IV) dioxide ($TiO_2$) is known to have the best photocatalytic property among $TiO_2$ material family. In some embodiments, the primary photocatalyst comprises rhombus-shape anatase titanium dioxide ($TiO_2$) and has a major axis 10-35 nm and a minor axis 3-6 nm. This rhombus-shape anatase $TiO_2$ has a much higher volume density than that of the standard spherical-shape anatase $TiO_2$. Therefore, when the rhombus-shape anatase $TiO_2$ is activated, it could generate a lot more activated photocatalytic particles than that of the spherical-shape anatase $TiO_2$, resulting a more effective disinfection against pathogens.

In some embodiments, the secondary metallic photocatalyst may include silver, gold, copper, zinc, nickel, cerium, or a combination thereof. It is foreseeable to use other metal elements as the secondary photocatalyst. The metallic photocatalyst not only contributes to the photocatalytic activity itself, but also enables the primary metal oxide photocatalyst to absorb spectral energy in the visible light wavelength and become photocatalytic active. In some embodiments, the photocatalyst layer is activatable by a visible light in a wavelength range greater than 400 nm. With this feature, the self-disinfecting photocatalyst sheet when used in an indoor environment can thus be photocatalytic active with a visible light emitted from an indoor light source and can self-disinfect its surface continually against the microbial.

The secondary metallic photocatalyst may contain one or two or even more metallic photocatalyst materials. In some embodiments, the secondary photocatalyst only comprises two metallic photocatalyst materials, a third metallic photocatalyst and a fourth metallic photocatalyst. In some embodiments, the third metallic photocatalyst comprises silver nanoparticles (NPs) and the fourth metallic photocatalyst comprises cerium NPs. Both silver NPs and cerium NPs help improve the photocatalytic activity of anatase $TiO_2$ when illuminated with a visible light. It is found that silver NPs themselves are effective in inhibiting bacteria under a visible light, whereas cerium NPs are effective in inhibiting viruses under a visible light. Having both silver NPs and cerium NPs as the secondary metallic photocatalyst would improve the self-disinfection effectiveness of the present disclosure under a visible light.

In some embodiments, the substrate material comprises a glass. Some of the cellphone screen protectors are made of soda lime glass or alkaline-aluminosilicate glass, and they can be made to be a very thin sheet. They would be good candidates for the substrate material of the present disclosure. A screen protector with a self-disinfecting photocatalytic surface provides the user of the cellphone a continual antimicrobial protection against any germs on the screen protector.

In some embodiments, the substrate material comprises a resin. The resin has been widely used for screen protector, packaging, and surface covering. Some widely used resin includes polyvinyl chloride, polyethylene, polyethylene terephthalate, polyurethane, thermoplastic polyurethane, polypropylene, polystyrene, silicone, and other thermoplastic and thermosetting resins.

A method for producing the present disclosure includes the following steps. Step 1 is a surface activation step. In Step 1, a low-temperature atmospheric plasma or a corona treatment is applied to the first side of the substrate material for improving the hydrophilic property of the substrate material. A substrate material such as glass or resin may have a low hydrophilic property by nature. It is difficult to coat water-based solution to the surface of glass or resin. By applying a low-temperature atmospheric plasma or a corona treatment to the substrate material, the hydrophilic property of the substrate material can be greatly improved for a short time for the subsequent coating with a water-based solution. The low-temperature atmospheric plasma may be an oxygen plasma or a nitrogen plasma. The time and the temperature of the atmospheric plasma application would depend on the substrate material. For example, the time is shorter and the temperature is lower when using an atmospheric plasma to surface-activate a resin substrate material, whereas the time is longer and the temperature is higher when using the atmospheric plasma to surface-activate a glass substrate material. In Step 2, a hydrophilic primer containing either carboxyl groups or carbonyl groups is applied on the first side of the substrate material. Acrylic resin, alkyd resin, and polyurethane are good candidates for the hydrophilic primer. Step 3 is a surface coating step. In Step 3 a water-based photocatalyst solution is sprayed on the first side of the substrate material evenly. The water-based solution comprises greater than 98 wt % in water and less than 2 wt % in the primary photocatalyst and secondary photocatalyst. The mass ratio of the primary photocatalyst to the secondary photocatalyst is 10:1 to 100:1. Step 4 is a curing step. A heat curing is applied to the substrate material sprayed with the water-based photocatalyst solution so that the substrate material binds the photocatalyst layer by either connecting the primary photocatalyst and/or the secondary photocatalyst through two oxygen atoms of the carboxyl group, or by forming hydrogen bonds between the carbonyl group and a surface hydroxyl group (OH⁻) of the primary photocatalyst. Step 5 is an optional step for coating an adhesive layer on the second side of the substrate material. The adhesive layer may comprise a pressure-sensitive adhesive (PSA) material or an electrostatic-enhancing agent.

EXAMPLE IMPLEMENTATIONS

Figure 4:
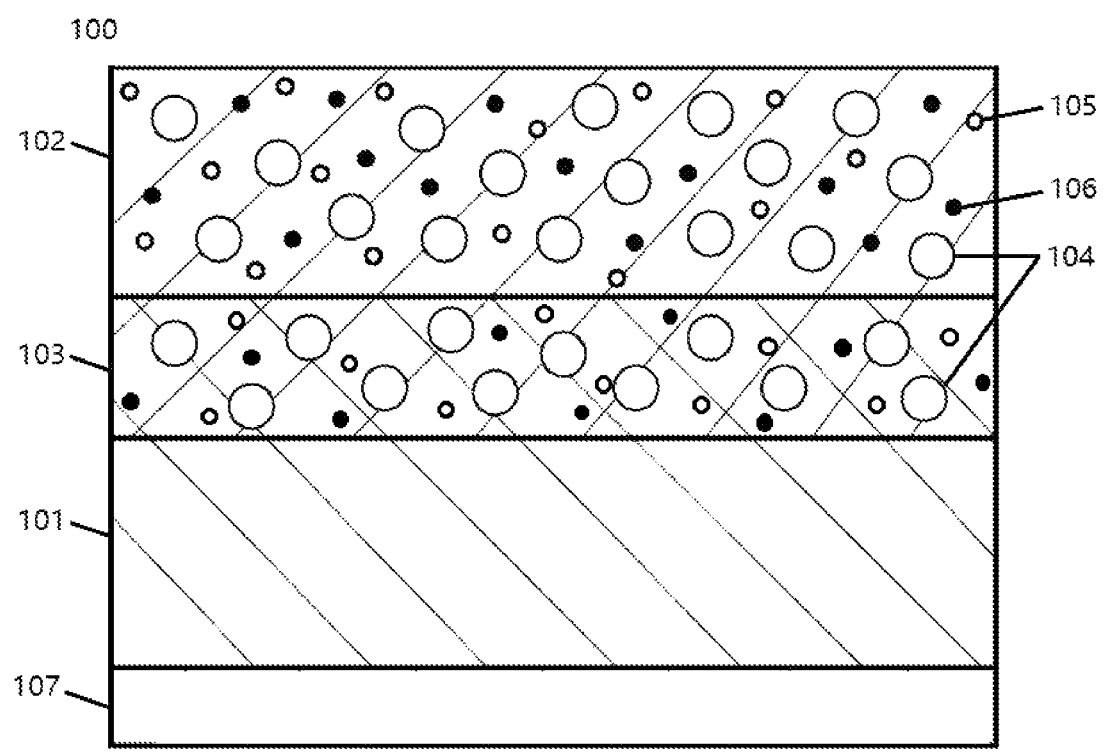
FIG. 4 schematically depicts a diagram of an embodiment of the present disclosure with adhesive coating on the second side of a substrate material.

In FIG. 4, an embodiment 100 of the present disclosure is shown. A photocatalyst layer 102 is coated over a substrate material, polyvinyl chloride (PVC) 101. The photocatalyst layer contains a primary metal oxide photocatalyst $TiO_2$ 104 and two secondary metallic photocatalysts, silver nanoparticles (NPs) 105 and cerium NPs 106. During the manufacturing process, a hydrophilic primer, acrylic resin, is used during the coating of the photocatalyst 102 onto the substrate material 101. As a result, on the boundary 103 where the photocatalyst 102 meets the substrate material 101, the bindings of a substrate material R via two oxygen atoms of a carboxyl group (COO) to an ion $Ti^{4+}$, an ion $Ag^+$, and an ion $Ce^{3+}$ (as shown in FIG. 1) may be seen. With the presence of the two secondary photocatalysts, the photocatalyst layer 102 is activatable by a visible light with a wavelength range greater than 400 nm. The second side of the PVC substrate material is coated with an adhesive layer 107 comprising a pressure-sensitive adhesive (PSA) material. With a PSA layer, the embodiment could be used as self-disinfecting window film, and it can be attached, removed, and even reattached to a glass window and provide self-disinfection protection for the glass window.

This embodiment is made firstly by treating the PVC substrate material 101 with an oxygen plasma at 50° C. Then one side of the plasma-treated substrate material PVC is treated with a hydrophilic primer, acrylic resin, followed by spraying with a water-based $TiO_2$ solution that also contains silver NPs and cerium NPs. The $TiO_2$ is rhombus-shape anatase titanium dioxide and has a major axis of 10-35 nm and minor axis of 3-6 nm. The $TiO_2$, silver NPs, and cerium NPs, together has less than 2 wt % of the solution, and the water has 98 wt % of the solution. The mass ratio of the secondary photocatalysts, silver NPs and cerium NPs, to the primary photocatalyst $TiO_2$ is 30:1. The substrate material being sprayed with a water-based $TiO_2$ solution goes through a heat curing process for 30 minutes at 150° C. Lastly, the second side of the PVC substrate material is coated with an adhesive layer comprising a pressure-sensitive adhesive (PSA) material.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A self-disinfecting photocatalyst sheet, comprising:
a substrate material with a first side and a second side opposite the first side; and
a photocatalyst layer comprising a primary photocatalyst and a secondary photocatalyst, wherein the photocatalyst layer is activatable by a visible light in a wavelength range greater than 400 nm;
a primer containing either carboxyl groups or carbonyl groups between the first side of the substrate material and the photocatalyst layer,
wherein:
the primary photocatalyst comprises a metal oxide photocatalyst, which is anatase titanium dioxide having a rhombus-shape comprising a major axis 10-15 nm and a minor axis 3-6 nm,
the secondary photocatalyst comprises a metallic photocatalyst, selected from silver, gold, copper, zinc, nickel, cerium, or a combination thereof,
a mass ratio of the primary photocatalyst to the secondary photocatalyst is between 10:1 to 100:1,
the secondary photocatalyst absorbs a visible light energy, transfers the energy to the primary photocatalyst, thus activating the primary photocatalyst as the primary disinfecting agent, and
the substrate material binds the photocatalyst layer by either:
connecting either or both of the primary photocatalyst and the secondary photocatalyst through two oxygen atoms of a carboxyl group (COO) comprising the primer, or
forming hydrogen bonds between the carbonyl group and a surface hydroxyl group (OH—) of the primary photocatalyst.

2. The self-disinfecting photocatalyst sheet of claim 1, further comprising an adhesive layer which is coated on the second side of the substrate material.

3. The self-disinfecting photocatalyst sheet of claim 1, wherein the secondary photocatalyst further comprises a third metallic photocatalyst and a fourth metallic photocatalyst with no other metallic photocatalysts, and wherein the third metallic photocatalyst and the fourth metallic photocatalyst are selected from silver, gold, copper, zinc, nickel, and cerium.

4. The self-disinfecting photocatalyst sheet of claim 3, wherein the third metallic photocatalyst comprises silver nanoparticles (NPs) and the fourth metallic photocatalyst comprises cerium NPs.

5. The self-disinfecting photocatalyst sheet of claim 1, wherein the substrate material comprises a glass.

6. The self-disinfecting photocatalyst sheet of claim 1, wherein the substrate material comprises a resin.

* * * * *